United States Patent [19]

Lyman

[11] 4,282,434

[45] Aug. 4, 1981

[54] RADIATION MEASUREMENTS ON MINERAL SLURRIES

[75] Inventor: Geoffrey J. Lyman, Taringa, Australia

[73] Assignee: The University of Queensland, St. Lucia, Australia

[21] Appl. No.: 964,307

[22] Filed: Nov. 28, 1978

[30] Foreign Application Priority Data

Nov. 28, 1977 [AU] Australia .................... PD2575

[51] Int. Cl.³ .............. G01V 23/00; G01N 5/00; B01D 19/00
[52] U.S. Cl. ................................ 250/359; 250/255; 55/55
[58] Field of Search ............... 250/255, 256, 268, 301, 250/304, 308, 358 R, 359, 360, 432 R; 73/153, 155, 32 R; 55/55

[56] References Cited

U.S. PATENT DOCUMENTS

| 2,437,935 | 3/1948 | Brunner et al. ............ 250/358 R |
| 3,031,571 | 4/1962 | Fearon ........................ 73/153 |
| 3,518,167 | 6/1970 | Klett ............................ 55/55 |
| 4,002,053 | 1/1977 | Hayakawa ................. 73/32 R |
| 4,134,294 | 1/1979 | Patillet et al. ............... 73/155 |

FOREIGN PATENT DOCUMENTS 1207664 12/1965 Fed. Rep. of Germany ......... 73/32 R

Primary Examiner—Davis L. Willis
Assistant Examiner—Janice A. Howell
Attorney, Agent, or Firm—Schwartz, Jeffery, Schwaab, Mack, Blumenthal & Koch

[57] ABSTRACT

A method of radiation measurements on slurries where the slurry is pumped to a pressure where the volume of gases in the form of gas-bubbles is reduced below a level where the gases effect the radiation counts. The slurry pressure is raised to a pressure in the range of 100 p.s.i. to 500 p.s.i. (690 kPa to 3.5 Mpa) absolute using a positive displacement pump.

14 Claims, 4 Drawing Figures

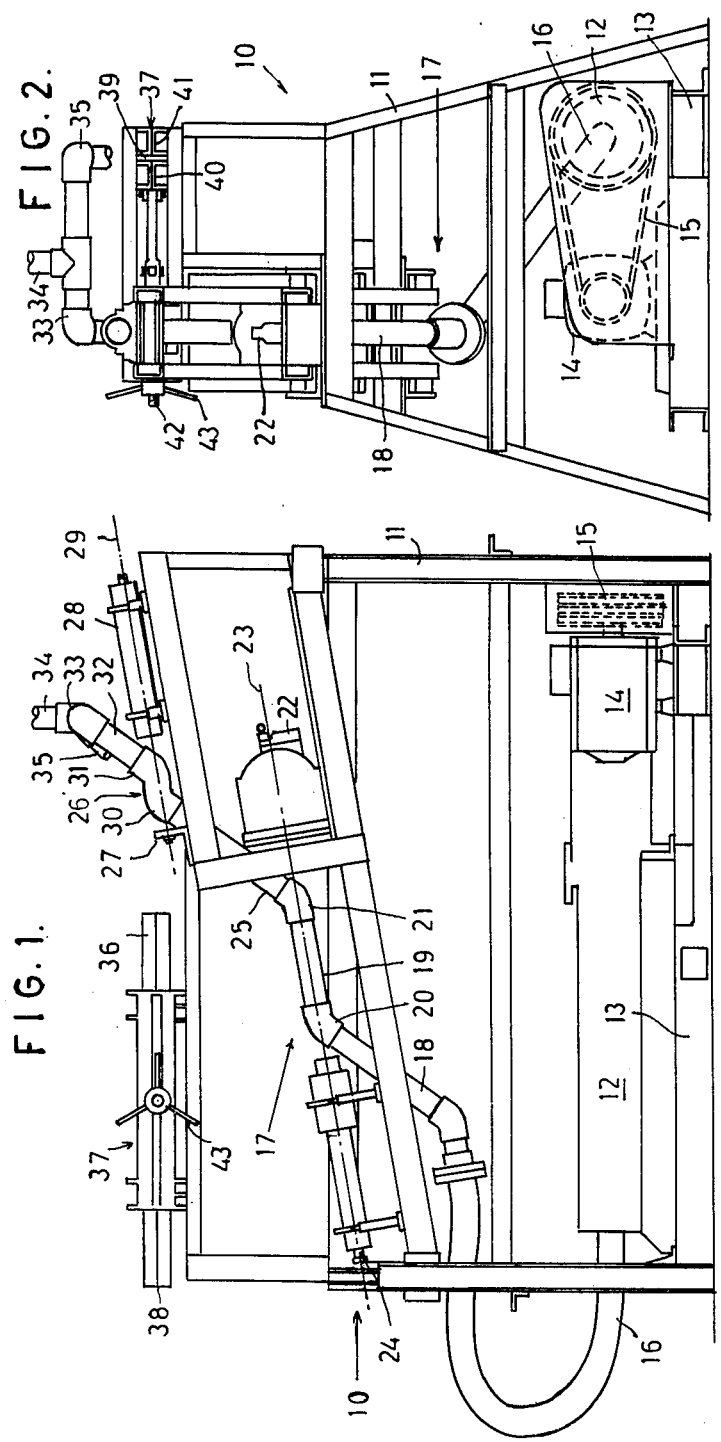

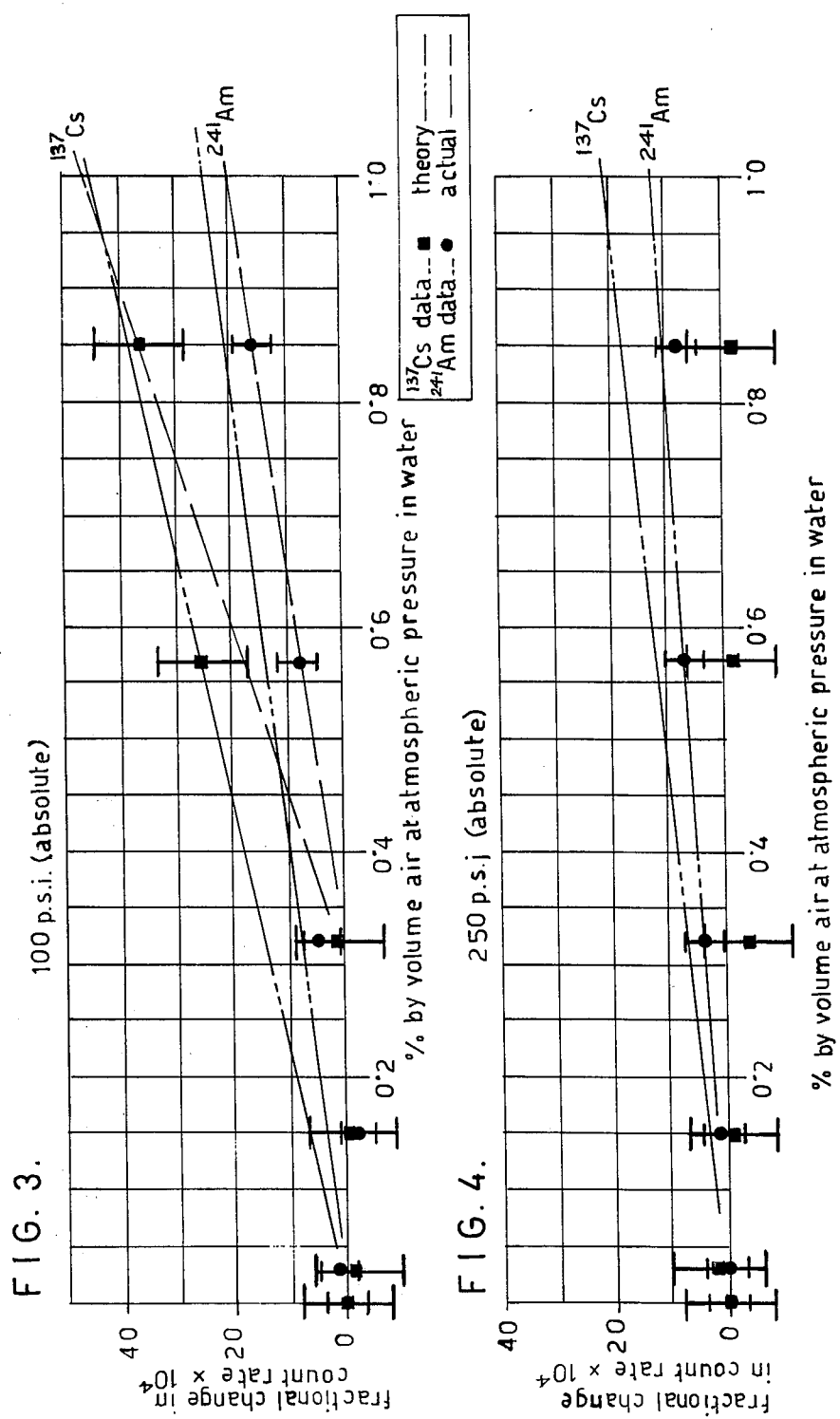

RADIATION MEASUREMENTS ON MINERAL SLURRIES

BACKGROUND OF THE INVENTION

1. Field of the Invention

This invention relates to apparatus and techniques for improving the accuracy of radiometric measurements of properties of solid-liquid suspensions. In particular, this invention relates to improvement in the accuracy of measurement of gamma- or x-ray transmission through, or scatter from, suspensions (slurries) of minerals (including coal) in water, where the objective of such measurements is to determine slurry density or elemental composition, for the purpose of controlling industrial mineral processing operations.

Data from which slurry density or slurry elemental composition may be reduced can be obtained by measuring the intensity of gamma- or x-electromagnetic radiation transmitted through, scattered from or excited from a mineral slurry. Under circumstances where the slurry is conveyed in equipment containing air or other gases, measurement accuracy can be impaired by the entrainment of variable quantities of bubbles of these gases in the slurry, where these variable quantities of gas are present at the point where the radiation measurement is made. The extent to which measurement accuracy is impaired is proportional to the volume fraction of gas in the slurry.

Inaccuracies of measurement due to the presence of gases, usually air, in slurries are usually minimised as far as possible by conveying the slurry through a series of units of equipment, such as low-head pump-sump units, so that any air present tends to be present at a constant volumetric concentration. (By "low-head", it is meant that the pressure-head of the pump is only sufficient to move the slurry and the pressure may be in the region of 15 pounds per square inch (p.s.i.) (103.4 kPa) absolute.)

However, the percentage of air in the slurry is still significant and may for example be in the range of 1%–5% by volume.

2. Description of the Prior Art.

One solution which has been proposed to remove the gas is a method of vacuum de-gassing where the slurry sample is pumped into a vacuum chamber, most of the gas comes out of the slurry, and the nearly gas-free slurry is then passed through a measuring zone. The solution has a number of problems, particularly in practical application in an industrial plant. Vacuum techniques are difficult for the operator with the need to keep the evacuated space effectively sealed and the difficulty of removing the slurry therefrom. This method is only suitable for very small sample flow and very fine materials.

It is extremely difficult to accurately measure the amount of gas in a slurry. In the laboratory, a gas-free calibration slurry is prepared and readings are taken as measured quantities of gas are introduced into the slurry. By comparing the radiation counts at the various gas levels with the counts from the slurry under consideration, the volume of gas in the slurry can be determined. The accuracy of this determination depends on the degree in which the calibration slurry is initially gas free. In addition, due to gravitational effects, the gas added to the calibration slurry forms bubbles which rise out of the slurry, affecting the results.

BRIEF SUMMARY OF THE INVENTION

With the present invention, the volume of gas does not have to be accurately measured, provided that the volume is below the level at which the gauge will operate satisfactorily.

It is an object of the present invention to reduce the effect of the gas in the slurry to a level where it has an insignificant effect on the radiation measurements obtained.

It is a further preferred object to provide a gauge for carrying out the method hereinbefore described.

Other objects will become apparent to the skilled addressee from the following description.

In one aspect, the invention resides in a method of radiation measurement in slurries including the steps of:
(a) raising the pressure of the slurry to reduce the volume of gas present as bubbles therein below a predetermined level;
(b) passing the slurry under pressure through a measurement zone; and
(c) measuring the radiation characteristics of the slurry.

Preferably the slurry is raised to a pressure where the volume of gas bubbles present both by dissolution of gas in the slurry and by compression is below the operating limit of the gauge.

Preferably the pressure of the slurry in the range of 100 p.s.i. to 500 p.s.i. (690 kPa to 3.5 MPa) absolute, with a preferred pressure of 300 p.s.i. (2 MPa) absolute. For example, where the slurry has 2% by volume of gases at atmospheric pressure (approximately 15 p.s.i. (103 kPa) absolute) and the gauge will operate satisfactory with 0.1% by volume gas (free as bubbles), increasing the pressure to 300 p.s.i. (2 MPa) will compress the gas bubbles so that the slurry has 0.1% by volume of gas (free as bubbles—assuming no increase in solubility and no chemical reaction occurs between the slurry and the gas).

In a second aspect, the invention resides in gauge for radiation measurements on mineral slurries including:
pumping means to raise the pressure of the slurry to reduce the volume of gas bubbles therein;
throttling means to regulate the pressure of the slurry; and
a measurement zone where the radiation characteristics of the slurry are detected.

Preferably the pumping means is a positive-displacement pump having a maximum output pressure of 500 p.s.i. (3.45 kPa) absolute.

Preferably the throttling means is a pressure control valve comprising a section of hydraulic hose compressed laterally in a press to regulate the pressure drop in the hose and thereby control the slurry pressure.

Preferably the measurement zone includes a section of acrylonitrile and butadiene-styrene (ABS) thermoplastic piping having 1, but preferably 2, "S-bend" sections. Preferably the radiation is transmitted along the axis of the piping, entering and leaving the elbows of the "S" in the "S-bend" sections.

BRIEF DESCRIPTION OF THE DRAWINGS

To enable the invention to be fully understood, a preferred embodiment will now be described with reference to the accompanying drawings, in which:

FIG. 1 shows a side view of the gauge;
FIG. 2 shows an end view of the gauge;

FIG. 3 is a graph showing the variation in count rate-v-percentage of gas in the slurry at 100 p.s.i. (690 kPa); and FIG. 4 is as for FIG. 3 at 250 p.s.i. (1.725 MPa).

DETAILED DESCRIPTION OF THE PREFERRED EMBODIMENT

Referring to FIGS. 1 and 2, the apparatus 10 has a frame 11 which may be portable or fixed to a floor.

A positive displacement pump 12 is mounted on a base 13 and is driven by an electric motor 14 via a belt-and-pulley drive arrangement 15. In the experimental stage, the pump 12 had a capacity of approximately 25 g.p.m. (110 liters/minute) and a discharge pressure of 300 p.s.i. (2 MPa). Incoming slurry from a sump or process line (not shown) is fed into the pump 12, where the pressure in the slurry is raised to a pressure that is adequate to dissolve and compress the gases present in the slurry to a volume (e.g. less than 0.1% which will not impair the measurement accuracy unduly.

From the pump, the slurry under pressure is passed through a length of connection hose 16 to the measurement zone 17. The length of the hose 16 is selected to be sufficient to allow all or most of the gases under pressure to dissolve into the slurry.

The slurry flows from hose 16, through a connecting pipe 18, to the first "S" bend section of ABS thermoplastic piping 19 having an inlet elbow 20 and an outlet elbow 21, also formed of ABS thermoplastic material. In the experimental stage, the piping 19 and elbows 20, 21 had an external diameter of approximately 2 inches (5 cm) and a wall thickness of 0.2–0.4 inches (0.5–1.0 cm).

A caesium ($^{137}$Cs) source 22 transmits gamma-radiation through the slurry along line 23 coaxially with the longitudinal axis of the piping 19. The radiation enters the slurry through outlet elbow 21, passes along piping 19 and exits via inlet elbow 20 to be detected by a scintillation counter 24 coaxial with the line 23. The counts recorded by the scintillation counter 24 is relative to the mean density of the slurry.

From the outlet elbow 21, the slurry flows through a second connecting pipe 25 to the second "S" bend section of ABS piping 26. An Americium ($^{241}$AM) source 27 and a second scintillation detector 28 are aligned co-axially with the axis 29 of the second section of piping 26. The gamma-radiation from the $^{241}$AM source enters the piping 26 (and the slurry) via the inlet elbow 30 and exits from the piping (and the slurry) via outlet elbow 31. The counts recorded by the second scintillation counter 29 is determined by (i) the slurry density and (ii) the composition of the slurry (e.g. to the coal-/ash ratio).

A section of pipe 32 connects the second section of piping 26 to a cross-pipe 33. One outlet 34 from the cross-pipe, which is normally closed, leads to a bypass-pipe. The second outlet 35 is connected by a pipe (not shown) to the inlet 36 of the pressure-control valve 37.

The pressure control valve, having inlet 36 and outlet 38, incorporates a section of hydraulic hose 39 clamped between the two platens 40, 41 of a mechanical press, the distance between the platens and thereby the pressure drop in the hose 39, being controlled by a screw threaded shaft 42 moved by a wheel 43. As shown in FIG. 2, rotation of the wheel 43 to move the shaft 42 to the right reduces the distance between the platens and increases the pressure drop in the hose 39 and thereby, the pressure on the slurry. The pressure drop in the hose 39 is set to ensure the pressure in the slurry is sufficient to reduce the percentage of gas in the form of bubbles in the slurry below the desired volume.

The operation of the gauge is comparatively simple. The slurry under test is drawn from the sump and pumped to the required pressure by the pump 12. The slurry, under pressure, flows through the connection hose 16 and all or most of the gas present in the form of bubbles becomes dissolved in the slurry before the measuring zone 17 is reached. The gamma-radiation from the $^{137}$Cs source is transmitted through the slurry in the first "S"-bend section 19 to be detected and counted by the scintillation detector 22. From there the slurry flows to the second "S"-bend section 26 where the gamma-radiation from the $^{241}$AM source is transmitted therethrough and detected and counted by the scintillation detector 28. The slurry flows through cross-pipe 33 and out through the pressure-control valve.

The pressure control valve has a number of advantages over known metal control valves e.g. of the bolt or gate-type. With the known valves, the orifice must be small to cause the pressure build up in the slurry. Because of the abrasive nature of slurries, the orifice(s) rapidly wear and the pressure is reduced, requiring replacement of the valve. Secondly, it would be necessary to use a number of such known valves to raise the slurry pressure to the desired level, each liable to blockage. With the present valve, the abrasive effects of the slurry are minimised and the pressure drop across the valve is over a relatively large distance, so only one such valve is required and the chance of blockage is markedly reduced. Should the hydraulic hose 39 wear out, it can be easily and inexpensively replaced.

Referring to FIG. 3, a graph showing the fractional change in count rate against the percentage volume of air at atmosphere pressure in water shows the variation between the theoretical count rate and the actual count rate where the water is at a pressure of 100 p.s.i. (690 kPa) absolute.

As can be easily seen, when the volume of air present in the water is below approx. 0.33% any variation in the percentage of gas does not affect the count rate.

In FIG. 4, when the pressure of the water is increased to 250 p.s.i. (1.73 MPa) absolute, no variation of the count rate occurs if the volume of gas is below 0.1% by volume.

As discussed above, the pressure in the system can be raised to any value that is adequate to dissolve and compress the gases present in the slurry to a volume which will not impair measurement accuracy unduly. Optimum operating conditions depend upon the initial amount of gas (as a volume fraction) entrained in the slurry; the greater the initial volume fraction of gas, the greater the pressure required to compress the gas sufficiently to avoid errors. Mathematically, if the initial volume fraction of gas is $V_O$ and gas solubility in gram liter$^{-1}$ kPascal$^{-1}$ is S at a possible pressure $P_O$, the final volume fraction at pressure p is approximately (for small initial volume fractions)

$$\frac{p_0 V_0}{p} - S p_{go}\left(1 - \frac{p_0}{p}\right)$$

where $p_{go}$ is the gas density at pressure $p_O$. Clearly, the higher the pressure, the lower the final volume fraction.

Various changes and modifications may be made to the arrangement described without departing from the scope of the present invention.

I claim:

1. A method of radiation measurements on continuously moving slurries including the steps of:
   (a) raising the pressure of the moving slurry to reduce the volume of gas present as bubbles therein below a predetermined value;
   (b) continuously moving the slurry under pressure through a measurement zone; and
   (c) measuring the radiation characteristics of the slurry.

2. A method as claimed in claim 1 wherein: the slurry is raised to a pressure in step (a) in the range of 100 p.s.i. (690 kPa) to 500 p.s.i. (3.5 MPa) absolute.

3. A method as claimed in claim 2 wherein: the slurry is raised to a pressure of substantially 300 p.s.i. (2 MPa) absolute.

4. A method as claimed in claim 1 wherein: the volume of gas present in the slurry in the form of bubbles is less than 0.4% by volume of the slurry.

5. A method as claimed in claim 4 wherein: the volume of gas is less than 0.1% by volume.

6. A method as claimed in claim 5, wherein: the slurry is raised to a pressure in step (a) of substantially 300 P.S.I. (2 MPa) absolute.

7. A method as claimed in any one of claims 1 to 5 or 6 and further including the step of:
   (d) passing the moving slurry through a pressure-control valve downstream of said measurement zone.

8. A gauge for radiation measurements on continuously moving slurries including:
   pumping means for moving said slurry and for raising the pressure of the slurry to reduce the volume of the gas bubbles therein;
   means for regulating the pressure of said slurry; and
   means for measuring the radiation characteristics of said slurry located a selected distance from said pumping means.

9. A gauge as claimed in claim 8 wherein: the pumping means include a positive-displacement pump having a maximum outlet pressure of 500 p.s.i. (3.5 MPa) absolute.

10. A gauge as claimed in claim 8 or claim 9 wherein: the distance between the pumping means and the measuring means is selected to allow the gas bubbles to dissolve into the slurry.

11. A gauge as claimed in any one of claims 8 or 9 wherein: the pressure regulating means is a throttling pressure control valve downstream of the measuring means.

12. A gauge as claimed in claim 11 wherein the pressure-control valve includes: a section of hydraulic hose compressed laterally in a press to regulate the pressure drop in the hose.

13. A gauge as claimed in any one of claims 8 or 9 wherein said measuring means includes:
    at least one section of acrylonitrile-butadiene-styrene (ABS) thermoplastic piping having at least one "S-bend" section; and
    means for irradiating said slurry, the radiation being transmitted along the axis of the piping.

14. A gauge as claimed in claim 13, wherein: said pressure regulating means is a section of hydraulic hose compressed laterally in a press to regulate the pressure drop in the hose; and said selected distance between said pumping means and said measuring means is selected to allow the gas bubbles to dissolve into the slurry.

* * * * *